United States Patent [19]

Hsu et al.

[11] Patent Number: 4,524,233
[45] Date of Patent: Jun. 18, 1985

[54] PROCESS FOR THE PRODUCTION OF DIENES FROM ALDEHYDES

[75] Inventors: Wen-Liang Hsu, Akron; Neil A. Maly, Tallmadge; Barry A. Matrana; Robert W. Strozier, both of Akron; Lawson G. Wideman, Tallmadge, all of Ohio

[73] Assignee: The Goodyear Tire & Rubber Company, Akron, Ohio

[21] Appl. No.: 649,236

[22] Filed: Sep. 10, 1984

[51] Int. Cl.$^3$ .................. C07C 1/20; C07C 1/253
[52] U.S. Cl. .................. 585/606; 502/180; 502/202
[58] Field of Search ............. 585/606; 502/180, 202

[56] References Cited

U.S. PATENT DOCUMENTS 1,841,055  1/1932  Reppe .................................. 585/611
1,895,764  1/1933  Mittasch .............................. 502/202

FOREIGN PATENT DOCUMENTS 0080449   1/1983   European Pat. Off. .
1442617  10/1968   Fed. Rep. of Germany ...... 502/202
2163396   6/1973   Fed. Rep. of Germany ...... 585/606
48-00404  1/1973   Japan ................................. 585/606
1385348   2/1975   United Kingdom ................ 585/606
0721116   3/1980   U.S.S.R. ............................. 505/202

Primary Examiner—Delbert E. Gantz
Assistant Examiner—Helane Myers
Attorney, Agent, or Firm—D. O. Nickey

[57] ABSTRACT

This invention is directed to a process for the conversion of an aldehyde to a diolefin comprising contacting an aldehyde of 4 to 6 carbon atoms in the vapor phase at a temperature of 300° to 400° C. with a catalyst comprising boron phosphate wherein the initial molar ratio of phosphorous (P) to boron (B) (P/B) is less than 1.0 but greater than 0.6 which is in intimate admixture with from 0.1 to 10 weight percent graphite. More specifically, this invention is concerned with a process for the catalytic dehydration of 2-methylbutanal (2MBA) to isoprene in the vapor phase with a boron phosphate catalyst wherein the improvement comprises the use of a catalyst with a molar ratio of P/B of less than 1.0 but greater than 0.6 which contains from 0.1 to 10 weight percent graphite and 0 to 10 mole percent, based on moles of boron, of ammonia or an amine selected from the group consisting of mono-, di- and/or tri- alkyl amines of 1 to 10 carbon atoms.

11 Claims, 10 Drawing Figures

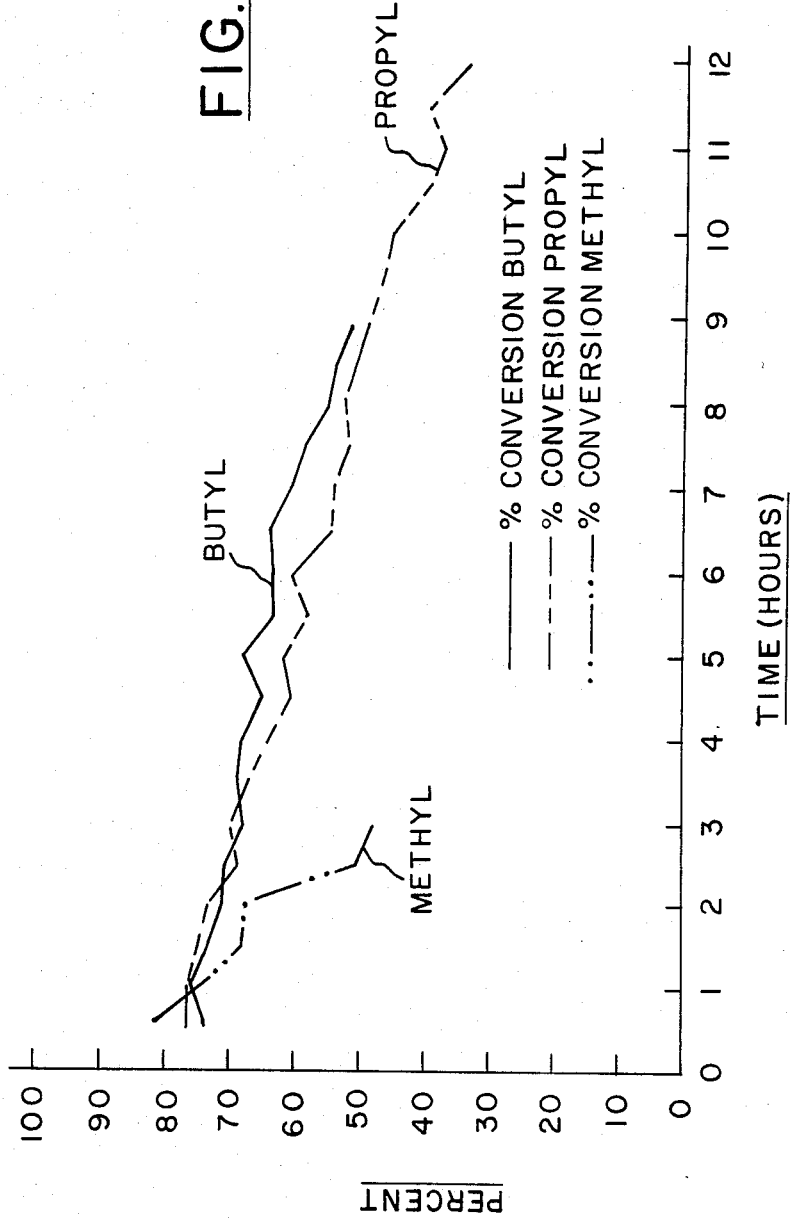

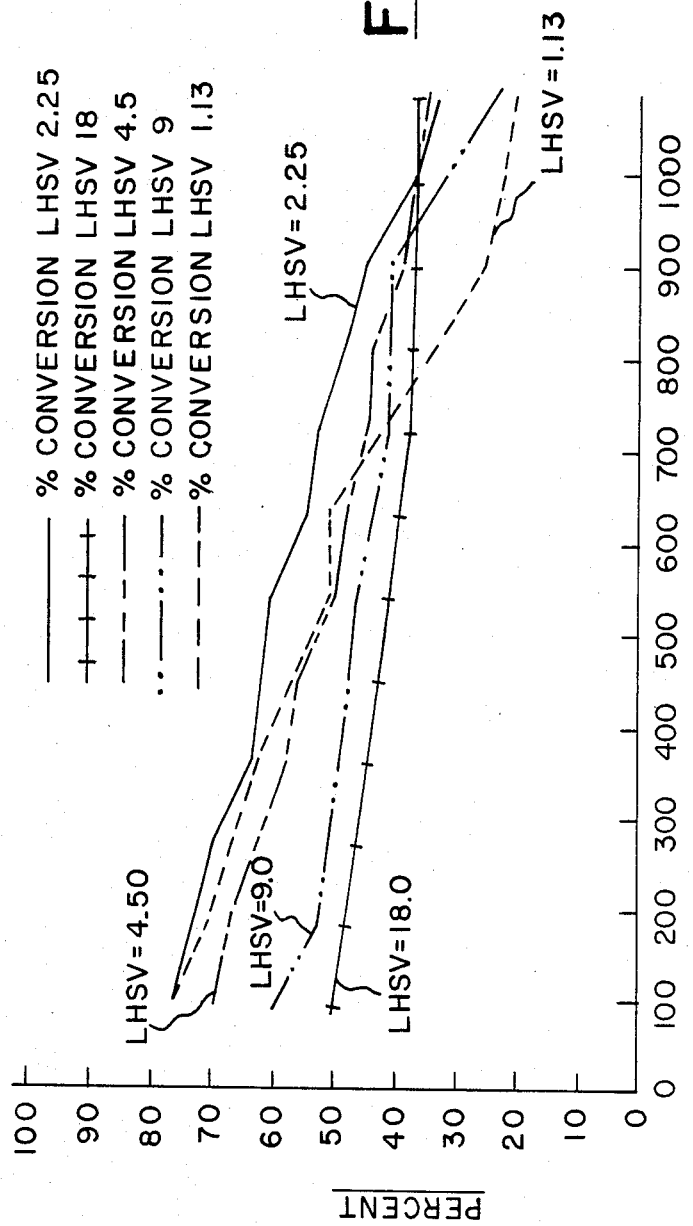

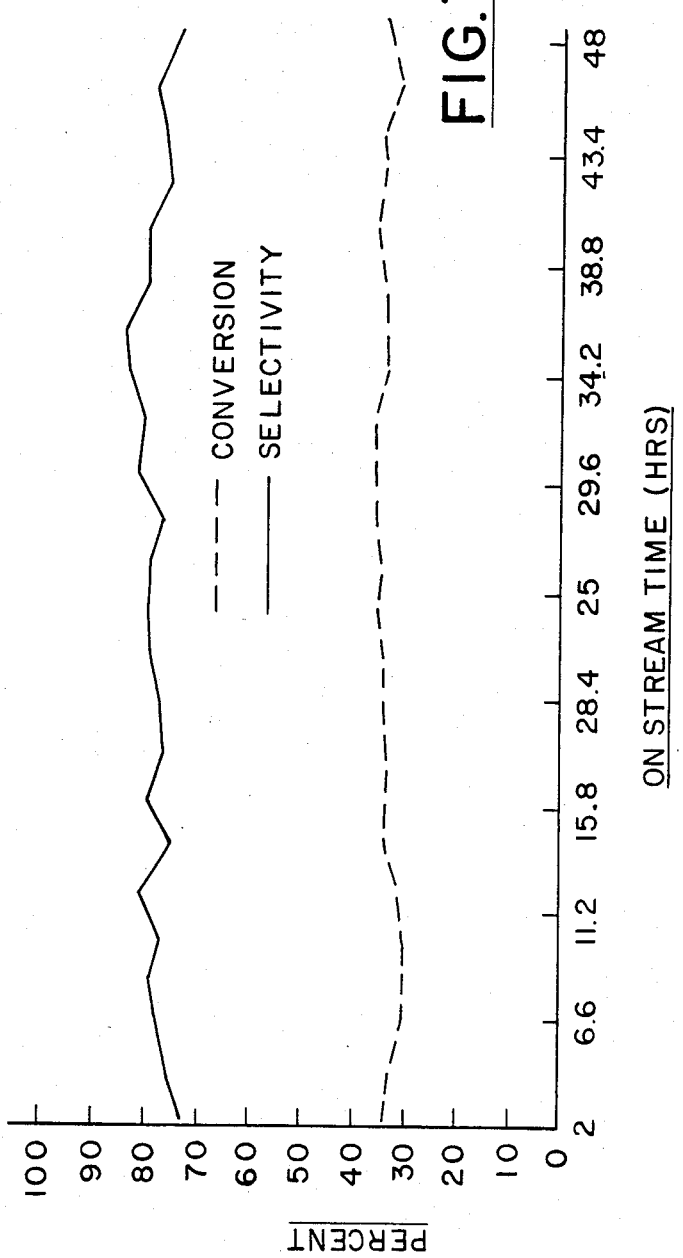

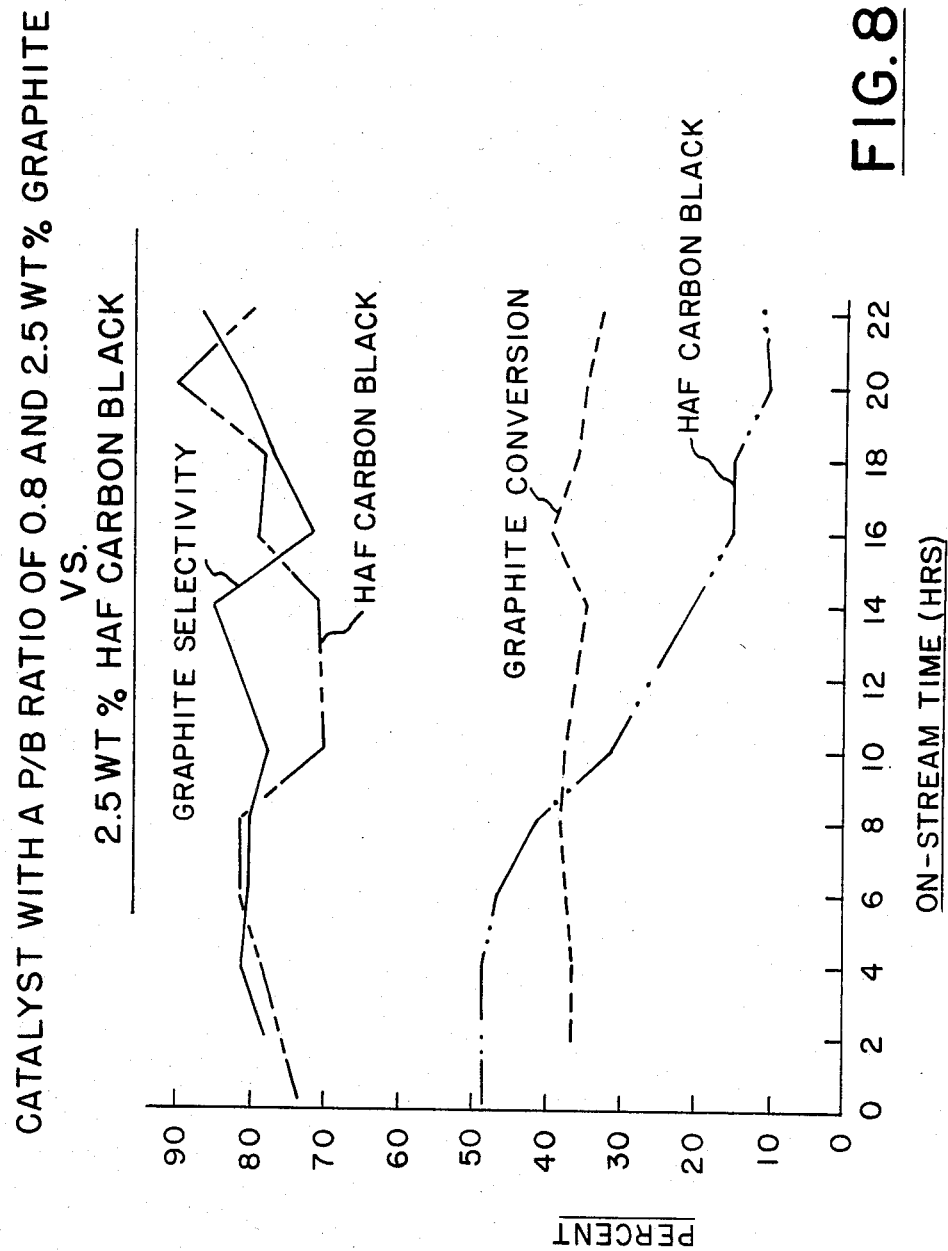

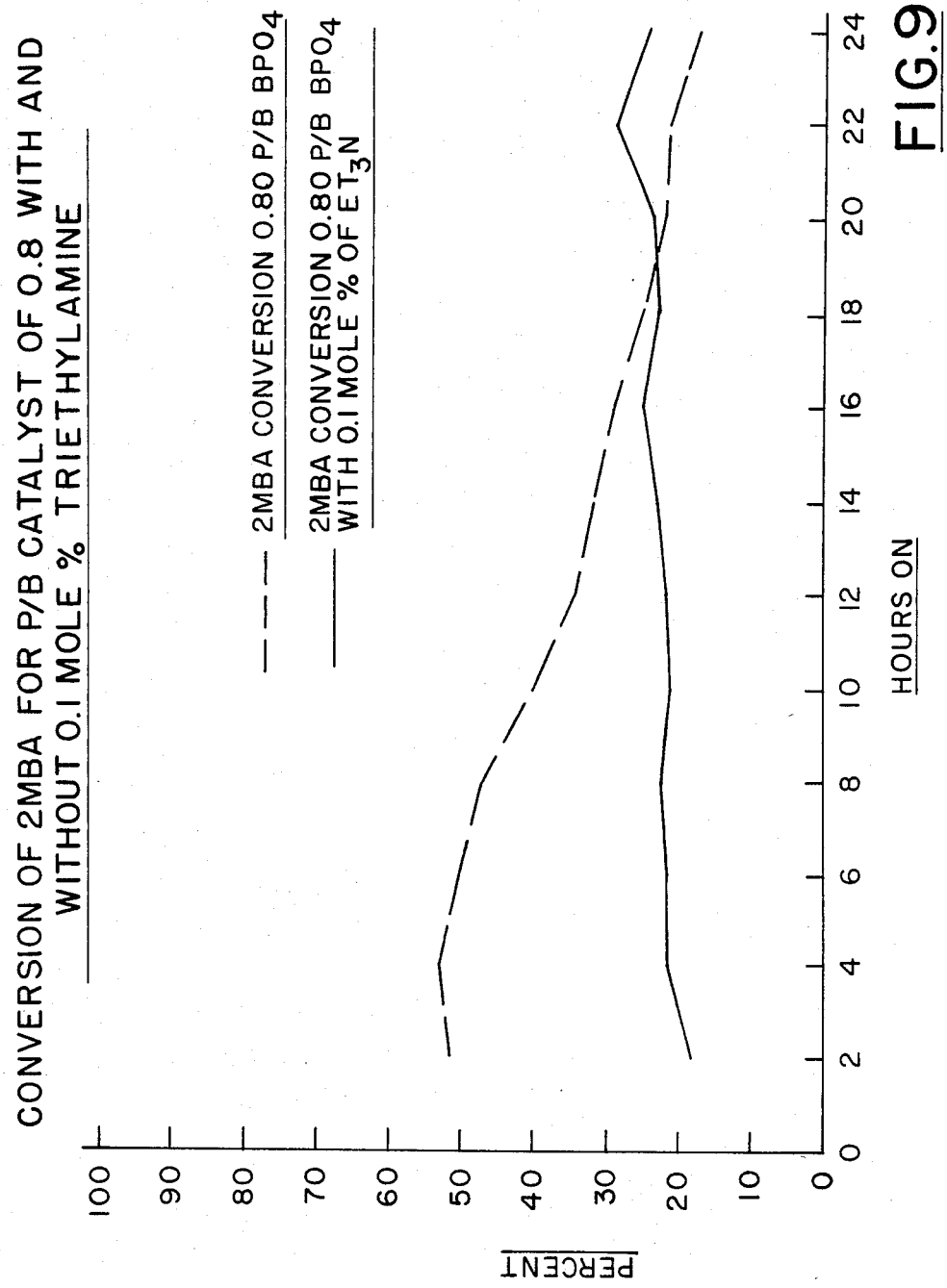

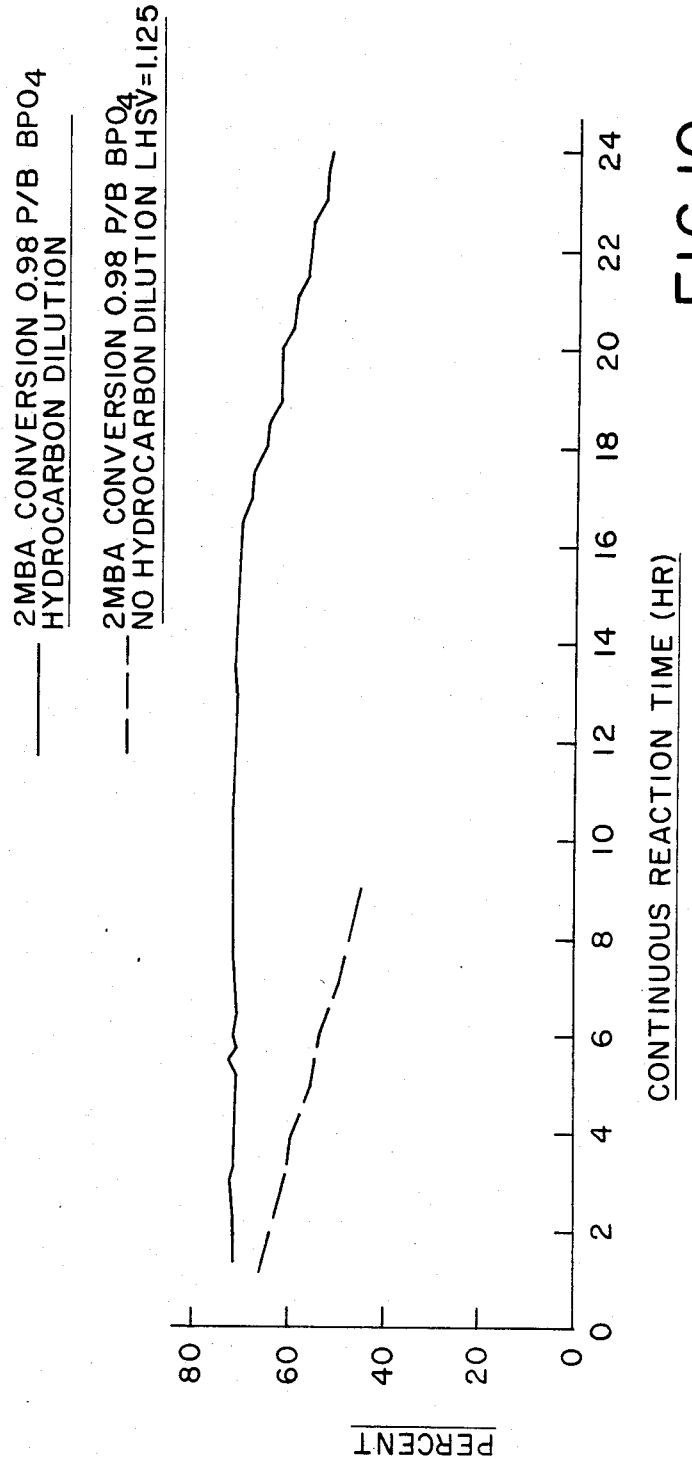

PROCESS FOR THE PRODUCTION OF DIENES FROM ALDEHYDES

TECHNICAL FIELD

This invention relates to a process for converting aldehydes to dienes. More specifically, this invention is concerned with a catalyst for the conversion of 2-methylbutanal (2MBA) to isoprene.

BACKGROUND ART

Dienes, especially isoprene, are useful as monomers for the manufacture of synthetic rubbers. Isoprene is primarily used to make cis-polyisoprene which is a stereospecific rubber having the same segmeric unit as natural rubber. Several fundamental processes have been used to construct the isoprene $C_5$ skeleton from smaller carbon units. These processes are not commercially accepted in that there are numerous problems associated with each particular synthesis route. One route involves condensing acetylene and acetone followed by hydrogenation and dehydration. Another route involves as a first step the reaction between formaldehyde and isobutylene, and in a subsequent step the intermediate derivative is catalytically cracked at elevated temperatures. See for example, French Pat. No. 1,294,716; Chem. Abstracts 57:15309.

European Patent Application No. 80449 based on U.S. application Ser. No. 315,803 discloses the synthesis of isoprene from linear butenes wherein mixed linear butenes are catalytically isomerized to a mixture of cis- and trans-butene-2, and then hydroformylating the butene-2 mixture to 2-methylbutanal (2MBA) in the presence of a homogeneous rhodium catalyst and organic ligand. The 2MBA is then dehydrated to isoprene in the presence of acidic heterogeneous catalysts at elevated temperatures. This European patent application discloses a preferred catalyst for the dehydration step as a boron phosphate which is described in British Patent No. 1,385,348. The dehydration reaction is endothermic, and under preferred conditions, the reaction is performed in the vapor phase over a fixed bed of catalyst at elevated temperatures from about 200° to about 400° C. This patent application, however, does not disclose the length of time the catalyst performs at such selectivities and conversions (lifetime). Commercial production of isoprene via the aldehyde dehydration route has not been established since the dehydration catalyst is known to have short lifetimes which limit its utility in commercial applications.

U.K. Patent No. 1,385,348 relates to the conversion of aldehydes to dienes with conjugated double bonds. This British patent recites that particularly preferred acid dehydration catalysts are mixed acid anhydrides, for example, boron phosphate, silicoborate or silicotitanate. In these mixed acid anhydrides the two acid components may be present in a stoichiometric ratio or, alternatively, one of the two components may be present in excess. Boron phosphate is particularly preferred. Further, U.K. No. 1,385,348 states that it is advantageous for the boron phosphate to contain an excess of from 1 to 10% by weight of phosphoric acid. The examples provided in the British patent utilizes a boron phosphate containing an excess of phosphoric acid. The examples recite results with conversions as high as 92.9% and selectivities as high as 68.4%. However, there is no discussion or information relating to the duration of such conversions and selectivities and/or the number of regenerations required during any particular time period.

U.K. Patent No. 2,093,060 relates to the preparation of substituted dienes, especially isoprene, from a corresponding carbonyl compound in which magnesium ammonium phosphate or its decomposition products are used as the dehydration catalyst. However, there is no data relating to the duration of catalyst activity.

A disadvantage associated with known catalysts to dehydrate aldehydes is that catalyst life depends on many factors which include catalyst composition and structure, catalyst activity, operating temperatures and coke deposition. Coke deposition is understood to denote coke (carbonaceous) deposits formed on the catalyst during the dehydration reaction. As stated earlier, no commercial process based on said technique has been developed so far, since there is no catalyst with selectivity and stability to justify a commercial process.

The use of boron phosphate as a catalyst for the dehydration of alcohols such as 2-butanol and 2-methyl-2-butanol is known. See Jewur and Moffat, *Journal of Catalysis*, 57, 167–176 (1979). The problems associated with an aldehyde dehydration are different and more difficult to overcome than those found in alcohol dehydrations. For example, the boron phosphate dehydration of 2-methyl-2-butanol yields only 2-methyl-2-butene and 2-methyl-1-butene, while dehydration of 2MBA yields primarily methylisopropylketone, 2-methyl-2-butene, 2-methyl-1-butene and isoprene. It is the production of the conjugated diolefin, isoprene, that makes the aldehyde dehydrations so difficult, since this highly reactive monomer is known to form dimers and/or polymerize in the presence of acid catalysts.

In addition, aldehydes such as 2MBA are known to undergo aldol condensation. This is a reaction between two molecules of an aliphatic aldehyde whereby a 3-hydroxyaldehyde is formed. Dehydration of the 3-hydroxyaldehyde results in the formation of terpenes, a highly undesirable by-product that can coke and deactivate the catalyst. Due to these and other differences, catalysts suitable for long term dehydration of alcohols have not been found acceptable for aldehyde dehydration.

One aspect of this invention is directed to the use of graphite which is in intimate physical admixture with the boron phosphate. Graphite has numerous known uses including utility as a carrier for catalysts and as a lubricant during catalyst pellet formation. See U.S. Pat. No. 1,841,055. The prior art does not suggest, disclose, or appreciate that the presence of graphite in a boron phosphate catalyst will unexpectedly enhance the viable lifetime of the catalyst in a 2MBA to isoprene dehydration. In addition to the P/B ratios and graphite, the instant invention is also directed to the ammonia or amine modification wherein the ammonia or amine is added during the boron phosphate preparation or subsequent thereto. The ammonia or amine is added in the range of 0.1 to 10 mole percent per mole of boron phosphate.

A portion of the instant invention is directed to a catalyst of high selectivity and low coke deposition in conjunction with extended catalyst lifetimes. The prior art does not suggest or disclose a specific catalyst or process for the dehydration of aldehydes to dienes which would be suitable for commercial application. The catalyst of this invention is boron phosphate wherein the molar ratio of P/B is initially less than 1.0 with from 0.1 to 10 weight percent graphite in physical admixture with or without 0.1 to 10 mole percent ammonia or amine.

DISCLOSURE OF THE INVENTION

There is disclosed a process for the conversion of an aldehyde of 4 to 6 carbon atoms to the corresponding diene which comprises contacting the aldehyde in the vapor phase at a temperature of from 200° to 400° C. with a boron phosphate catalyst, said catalyst is characterized in that the initial molar ratio of phosphorous (P) to boron (B) (P/B) is less than 1.0 but greater than 0.6 and wherein said boron phosphate is in intimate admixture with from 0.1 to 10 weight percent graphite.

There is also disclosed a process of preparing isoprene which comprises passing 2-methylbutanal in the vapor phase over a boron phosphate dehydration catalyst, the improvement comprising a catalyst which has an initial molar ratio of P/B of less than 1.0 but more than 0.6 which is in admixture with from 0.1 to 10 weight percent graphite and 0 to 10 mole percent ammonia or an amine selected from the group consisting of mono-, di- and tri-alkyl amines wherein the alkyl groups can range from 1 to 10 carbon atoms.

There is further disclosed a catalyst for the dehydration of an aldehyde to the corresponding diene, the improvement characterized in that the catalyst is boron phosphate with a molar ratio of P/B of less than 1.0 but more than 0.6 which is in admixture with from 0.1 to 10 weight percent graphite which has been treated with steam prior to use.

In addition, there is disclosed a process for the conversion of 2-methylbutanal (2MBA) to isoprene which comprises contacting 2MBA in the vapor phase at a temperature of from 200° to 400° C. with a boron (B) phosphate (P) catalyst, the improvement characterized in that (1) the boron phosphate catalyst is prepared by
  (a) combining phosphoric acid and boric acid and/or trialkylborate, wherein the alkyl group is from 1 to 6 carbon atoms;
  (b) at such molar ratios that the molar ratio of P/B is less than 1.0 but more than 0.6;
  (c) contacting the boron phosphate with from 0 to 10 mole percent based on moles of boron, ammonia or an amine, selected from the group consisting of mono-, di- and/or tri-alkyl amines wherein the alkyl group is from 1 to 10 carbon atoms;
  (d) admixing the boron phosphate with from 0.1 to 10 weight percent graphite based on total weight of the boron phosphate;
  (e) calcining the boron phosphate in air at a temperature of from 250° to 650° C. for 1 to 6 hours;
  (f) steaming the calcined boron phosphate at 200° to 300° C. for ½ to 10 hours;
(2) the 2MBA feed is diluted with from 0 to 80 weight percent with a solvent selected from the group consisting of pentane, hexane, heptane, octane and nonane; and
(3) the 2MBA is charged to the reactor at an LHSV of from 1.0 to 20.

It has been found that dienes with conjugated double bonds can be obtained with advantage from the corresponding aldehydes with the same number of carbon atoms by contacting the aldehyde with a boron phosphate dehydration catalyst wherein the ratio of P/B is less than 1.0, preferably less than 0.9 but more than 0.6 which is in intimate admixture with from 0.1 to 10 weight percent graphite.

Examples of the aldehydes suitable for use in the process according to the invention include 2-methylbutanal, 2,3-dimethylbutanal and 2- or 3-ethylbutanal. 2-Methylbutanal is particularly preferred.

The following materials are mentioned as examples of dienes which can be produced by the process according to the invention: 1,3-butadiene, isoprene, 1,3-hexadiene, 2,3 or 4-methyl-1,3-pentadiene, 2,3-dimethylbutadiene and 2-ethyl-1,3-butadiene.

The process according to the invention is generally carried out at a temperature from 200° to 400° C. with 275° to 350° C. being preferred.

Representative of the solvents which are useful for the 2MBA feed dilution are pentane, hexane, heptane, octane, nonane and other hydrocarbons which are miscible with 2MBA and will not interfere with the dehydration.

Dehydration of aldehydes by the process according to the invention can be carried out at ambient pressure, for example, by vaporizing the aldehydes and passing them over the catalyst with or without a carrier gas. Inert gases such as nitrogen, carbon dioxide or hydrocarbons, especially saturated hydrocarbons, have proved to be of particular advantage as carrier gases.

The instant invention can also be carried out under reduced pressure, in which case a reduced pressure of from 0.60 to 1.33 Pa below atmospheric pressure has been found acceptable. Compression pressures of from 2 to 10 bar, more particularly from 2 to 4 bar can be regarded as both suitable and adequate.

The dehydration catalysts, according to the invention, are boron phosphates wherein the initial molar ratio of P/B can range from 0.60 to 1.0, which is in admixture with from 1 to 10 weight percent graphite. Initial molar ratio means that the catalyst charged to the reaction or pretreatment vessel has a P/B ratio of less than one. It has been discovered that during the use or steam pretreatment of these catalysts, the ratio of P/B approaches, but never exceeds, 1.0. It also has been found that the catalyst of the invention can be advantageously pretreated with steam. For example, a catalyst with an initial P/B ratio of 0.8 is placed in the reactor or a suitable vessel and ambient pressure steam is passed over the catalyst at an LHSV of at least 2.0, preferably 2.25, for at least ½ hour. By an LHSV of 2.25 is meant 2.25 volumes of liquid water per volume of catalyst is passed to the preheater for vaporization and then over the catalyst. It will be demonstrated later that this catalyst, after use or pretreatment, is substantially different than a catalyst with an initial ratio of 1.0 or greater.

Useful high surface area catalysts can be synthesized by reacting phosphoric acid with a trialkylborate. These high surface area boron phosphate catalysts have surface areas based upon nitrogen absorption on the catalyst surface of up to 220 m²/g. Several different trialkylborates of 1 to 6 carbon atoms will react with phosphoric acid to prepare the high surface area boron phosphate catalyst. Boron phosphate catalysts with a 0.8 molar ratio prepared with trimethyl and tributyl borate were tested, and it was determined that the trimethyl catalyst deactivated much faster than the tributyl catalyst and also had a much lower isoprene selectivity and conversion after 1 hour. The catalyst prepared with a tributyl borate had conversions equivalent to a tripropylborate catalyst but with a somewhat lower isoprene selectivity. Thus, a high surface area boron phosphate catalyst prepared with tripropylborate is an aspect of the instant invention.

The catalyst of the instant invention can also be synthesized via the paste method. In the paste method the amount of reagent grade 85% phosphoric acid required to give the desired mole ratio is placed in a glass reactor, heated to 70° C. and powdered reagent grade orthoboric acid is added slowly with stirring. After six hours the heat is removed and the resultant paste is spread over the inner surface of a glass tube and is heated to 110° C. in air for 16 hours. The white solid is chipped from the tube and stored in tightly sealed glass bottles. Prior to use the sample was ground and sieved through a 20-35 mesh sieve.

The catalyst of this invention can also be ammonia or amine modified. Ammonia or amine modifications means the addition of ammonia or an amine during the boron phosphate preparation or subsequent to the preparation to moderate surface acidity. Suitable amines are alkyl amines such as triethylamine, tripropylamine, diethylamine, triisopropylamine, and the like, aromatic amines such as pyridine, aniline, and the like. The amine may be added during the boron phosphate preparation or to the preformed catalyst at levels ranging from 0 to 10 mole percent based on moles of boron. When adding the amine or ammonia, a solvent may be used to facilitate dispersion with the preformed catalyst. One skilled in the art will realize that ammonia may be added in the aqueous form as ammonium hydroxide.

The catalyst can be used both in piece form (pelletized), for example, in a fixed bed reactor, and also in a fluidized bed reactor and in the form as prepared or even applied to an inert supporting material.

The dimensions of the catalyst are governed by the type of reactor used. In cases where a tube reactor is used as a fixed bed reactor, a tube diameter of from 10 to 50 mm has proved to be of advantage. The reactor is thus packed with catalyst particles in the form of granules, cylinders, pellets or spheres with an average diameter of the individual particles of from 2 to 12 mm, more particularly from 4 to 8 mm. In the case of a fluidized bed reactor, the catalysts used for the process are in the form of catalyst particles with dimensions of from 20 to 200 microns, preferably from 40 to 80 microns.

Both types of reactors can be used with equal effect for the process according to the invention. Only the working up of the reaction products will determine the particular method adopted. The fixed bed reactor is preferably used in the instant process with or without the use of a carrier gas.

The graphite utilized in the present invention is characterized by a surface area of about 1 to about 1000 $m^2/g$. Suitable graphites useful in the instant invention include both the natural and synthetic varieties which are produced by heating petroleum coke to 3000° C. in an electric furnace. Graphite is added to the boron phosphate during the mixing of the phosphoric acid with the boric acid/alkyl borate or after the resulting material has been dried and sieved. It is preferred to combine the graphite with the boron phosphate after the paste has been dried and sieved but before the catalyst is pressed or extruded in the form of rods or pellets.

During the dehydration reaction, it has been found to be advantageous to recycle the secondary products formed back to the reaction. The dehydration of 2MBA is accompanied by the formation of ketones which can be converted by dehydration to the corresponding diene. This may be accomplished in the same reaction zone or in a second reaction zone so that there is substantially no loss of selectivity.

It has been found that dilution of the 2MBA feed to the catalyst with a hydrocarbon such as heptane may be advantageous. Dilution of the 2MBA feed at ratios of 0 to 80% weight percent with an inert hydrocarbon is suitable. One skilled in the art will appreciate that any solvent for 2MBA which does not interfere with or enter into the dehydration reaction would be appropriate.

An advantage of the process of the instant invention is that the mild reaction conditions enable both the starting material and the reaction product to be sparingly treated, and this is reflected in the high selectivity of the reaction.

The instant invention has proved to be advantageous in that lesser amounts of tar are formed during the dehydration. In the presence of catalysts previously used for aldehyde dehydrations, for example, an aluminum silicate or heretofore used boron phosphates, tar formation occurs to such an extent that after reacting for 30 to 60 minutes there is a substantial decrease in both activity and selectivity of the catalyst. In order to regenerate such coked catalysts, the deposits would have to be burned off and after several regenerations, the catalyst may be totally useless.

BRIEF DESCRIPTION OF DRAWINGS

The invention and the advances over the art are easily understood from the accompanying figures which are graphs that set out percent conversion and/or selectivities against reaction time for several experiments. The reactor system used to generate the data contained in the Figures is described infra. The experimental catalysts were prepared generally as described herein, placed in the reactor system and tested for conversion of 2MBA to isoprene. All the experiments were conducted at an LHSV of 2.25, at 275° C. and without hydrocarbon dilution unless otherwise noted.

FIG. 5: Conversions as a function of Alkyl Group—for a trialkyl borate high surface area preparations.

Figure 1:
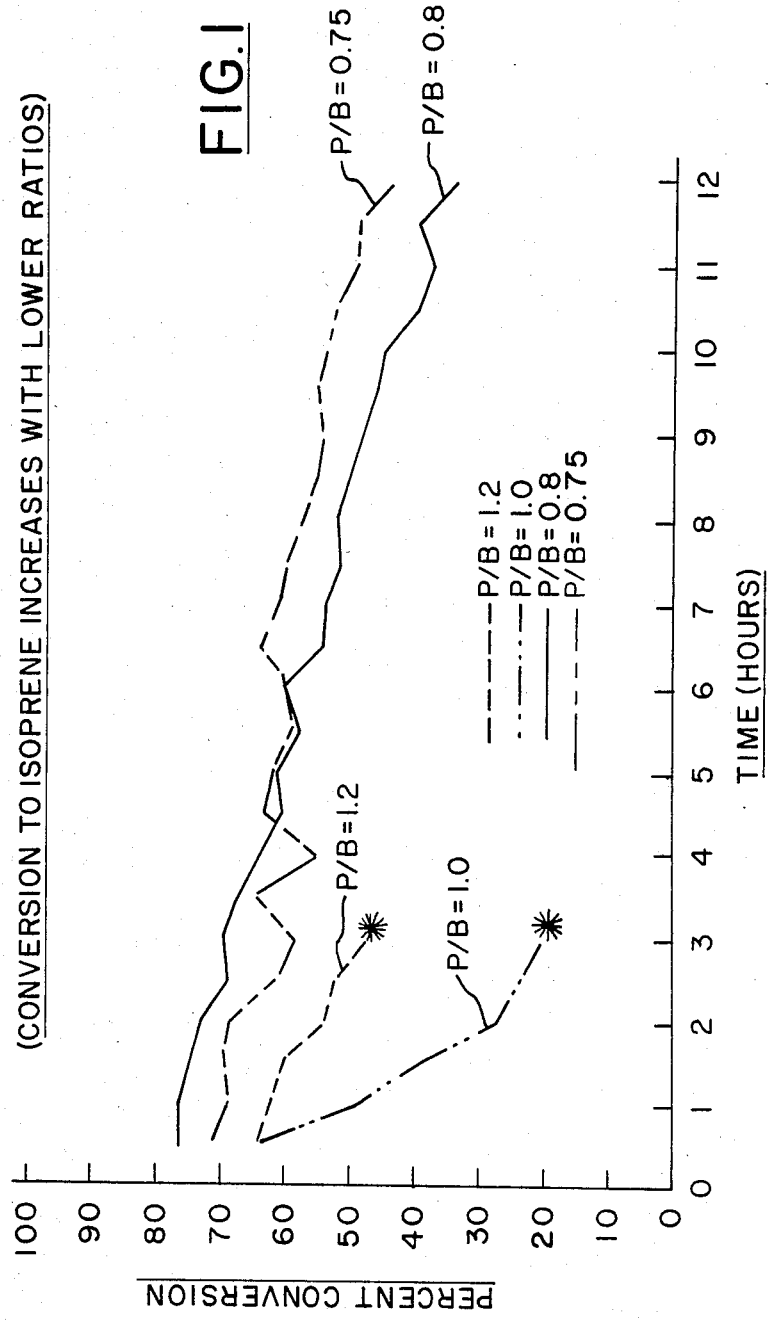
FIG. 1: Conversion of 2MBA with Different P/B Molar Ratios—sets out percent conversion against reaction time in hours for boron phosphate catalysts having a P/B molar ratio of 1.2, 1.0, 0.8 and 0.75. The catalysts were prepared using tripropyl borate and did not contain graphite. The graph readily points out that the higher P/B ratios of 1.0 and 1.2 deactivated (drop in conversion) much faster than the ratios of 0.75 and 0.8.
Figure 2:
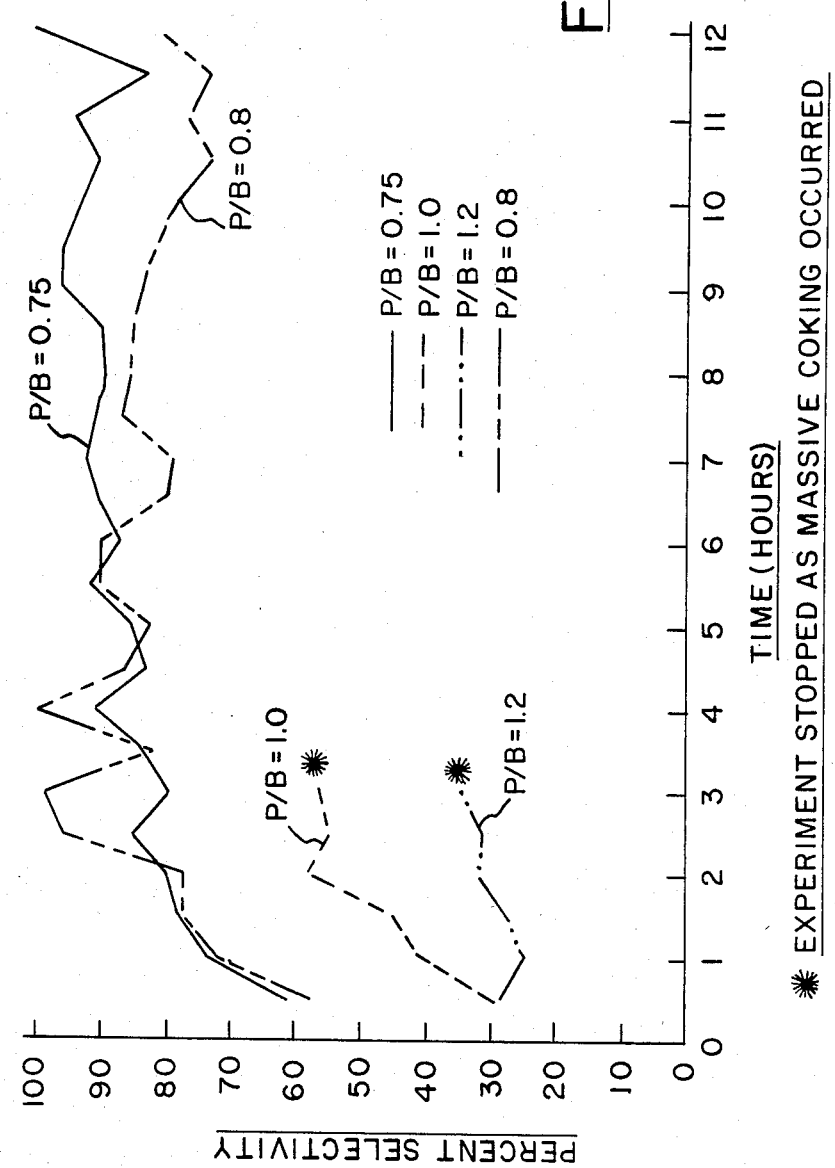
FIG. 2: Selectivity to Isoprene with Different P/B Molar Ratios—sets out percent selectivity against reaction time in hours for boron phosphate catalysts having P/B molar ratio of 1.2, 1.0, 0.8 and 0.75. The catalysts were prepared using tripropyl borate and did not contain graphite. It is evident that selectivity to isoprene is enhanced when the P/B ratio is less than 1.0.
Figure 3:
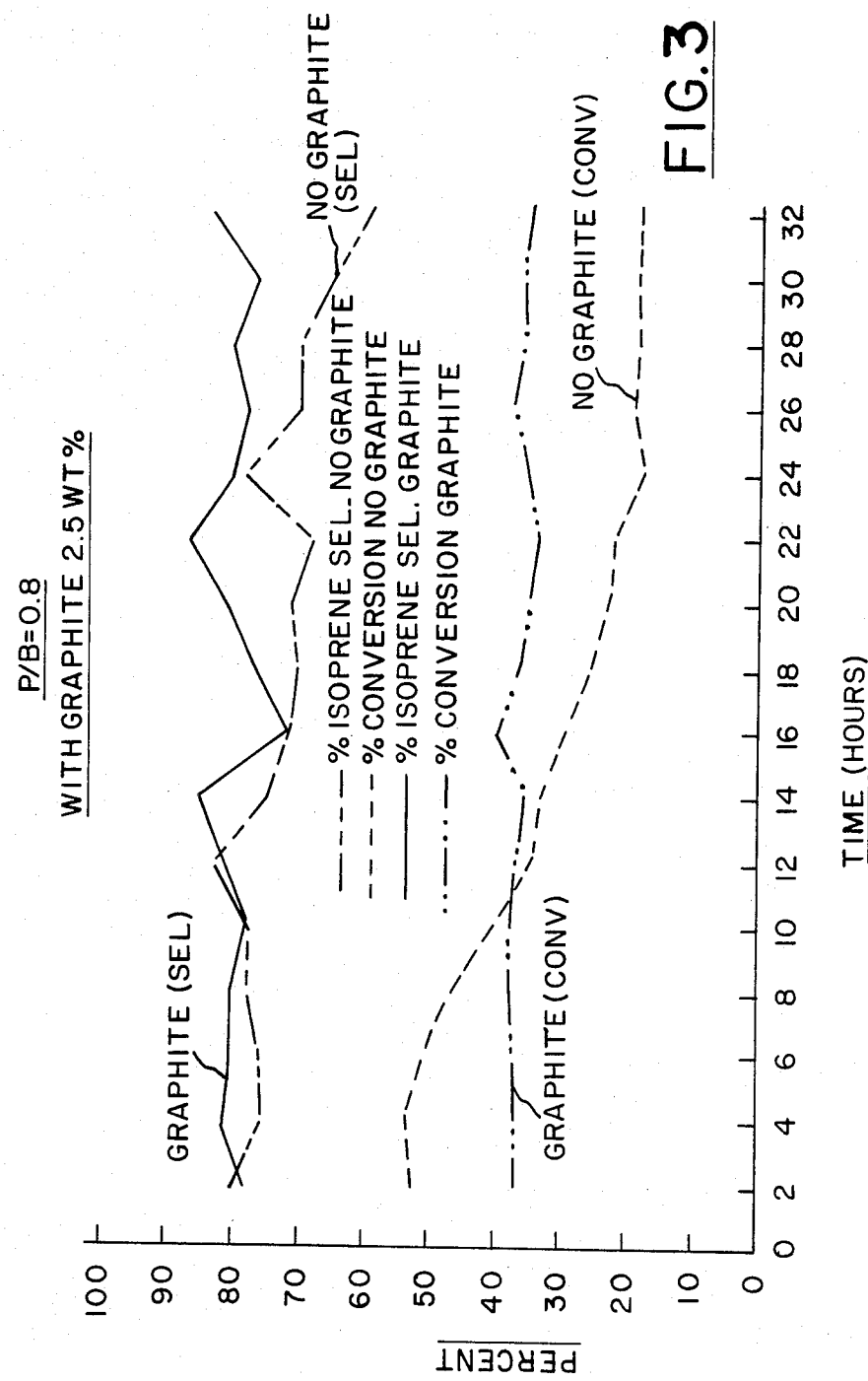
FIG. 3: Boron Phosphate Catalyst With and Without Graphite—sets out percent conversion and selectivity for two catalysts that were identical except that one catalyst contained 2.5% graphite by weight via the post paste method. This graph demonstrates the improved selectivity and conversion that can be obtained when incorporating graphite into a boron phosphate catalyst. More importantly, the graphite containing catalysts do not deactivate as rapidly, thus enhancing commercial utility.
Figure 4:
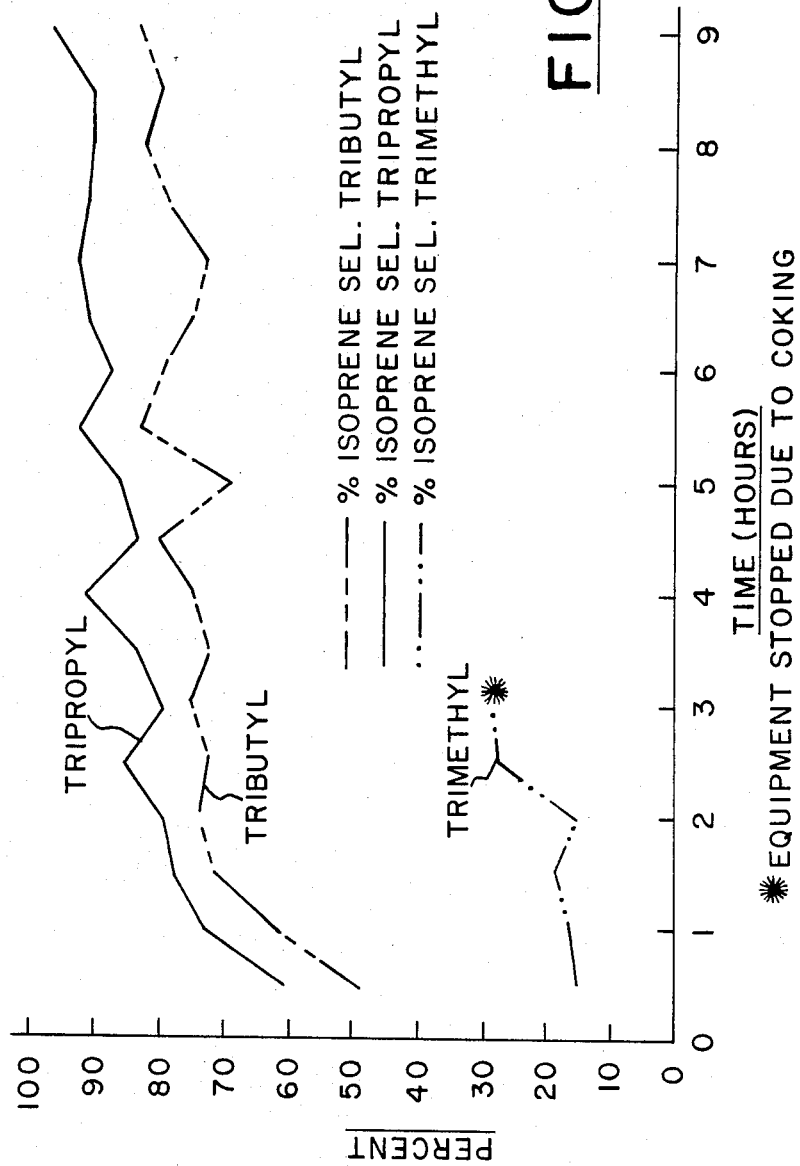
FIG. 4: Isoprene selectivity as a function of Alkyl Group—for trialkyl borate catalyst preparations.

From FIG. 4 and FIG. 5 it is evident that use of trimethyl borate in a catalyst preparation would be unsatisfactory.

FIG. 6: Conversion/Space Velocity comparison with a P/B ratio of 0.8, tripropyl borate preparation, no graphite. This demonstrates that a wide range of LHSV's is suitable.

FIG. 7: Catalyst with a P/B of 0.8 containing 1.25 wt % graphite. This graph demonstrates that inclusion of graphite provides extended periods of relatively constant conversion and selectivity which are desired in commercial applications.

FIG. 8: Catalyst with a P/B of 0.8 and 2.5 wt % HAF Black vs. the same catalyst with 2.5 wt % graphite. This demonstrates that the inclusion of carboneous materials other than graphite (i.e. HAF carbon blacks) will not enhance catalyst activity.

FIG. 9: Conversion of 2MBA for P/B Catalyst of 0.8 with and without 0.1 mole % triethylamine. The triethylamine was added during the paste preparation. This demonstrates that addition of the amine provides a catalyst that has greater stability with less coking.

FIG. 10: Effect of Hydrocarbon Dilution on conversion. The 2MBA feed was diluted 1 to 1 on a weight basis with heptane. The total feed (2MBA plus heptane) LHSV was 2.25, thus 2MBA feed alone was 1.125. This demonstrates that hydrocarbon dilution of the 2MBA feed provides a more constant conversion with time.

BEST MODE FOR CARRYING OUT THE INVENTION

Catalyst Preparation

High surface area boron phosphate catalysts were prepared by adding phosphoric acid (for example, 88.34 g of 85% acid) to a 500 ml resin kettle. The resin kettle was equipped with a paddle stirrer, oil bath, thermometer (in oil bath) and nitrogen inlet/exit. A trialkylborate such as tripropylborate (210.03 ml) was syringed into an addition funnel. After the resin kettle was purged with nitrogen, the trialkylborate was added slowly to the stirred phosphoric acid at room temperature. No exotherm was noted. After the addition was complete the oil bath was quickly heated to 120° C. and maintained at a temperature between 120° and 130° C. The nitrogen flow was increased and glass stoppers were removed to flush propanol (the resultant alcohol from the trialkyl borate) from the reaction mixture. After approximately 7 minutes the reaction mixture had thickened to a jelly-like consistency. The reaction temperature was maintained at about 130° C. until the mixture could only be stirred with difficulty. The thick gel was transferred to a 500 ml beaker and dried in a 65° C. vacuum oven overnight. The next day the finished catalyst was screened to a mesh of 35. The same procedure was used to prepare numerous catalysts of varying P/B molar ratios.

Using the paste method a glass reactor fitted with a stirrer, a condenser and heating mantle was charged with various amounts of boric acid and/or trialkylborate and phosphoric acid to achieve the desired P/B molar ratios. The mixed acids were heated to 70° C. and stirred for six hours with heating. The paste was removed and spread over the inner surface of a glass tube and heated to 110° C. in air for 16 hours. The white solid was chipped from the tube and sieved. The same procedure was used to prepare numerous catalysts of varying P/B ratios.

Portions of these catalysts were treated with ammonia or an amine at the paste stage or after sieving, and some were combined with graphite in the appropriate amounts and then extruded into rod forms or pressed into pellets.

EXPERIMENTAL

Calcination—Steam Treatment

The boron phosphates prepared as described above may be calcined or steam treated prior to use in the dehydration reaction or may be used as is, after drying. Steam treatment can be conducted in a separate vessel or in the reactor. When using the reactor, water is feed to the preheater at a rate of 1.5 to 2.5 volumes liquid water per volume of catalyst per hour and passed over the catalyst at ambient pressure for at least half an hour and up to 6 hours. This steam treatment is similar to what happens to a non-steamed catalyst during the first hours of a dehydration run, namely the P/B ratio approaches but does not exceed 1.0. It has been discovered that steaming a catalyst with a P/B ratio of 0.8, for example, leaches the excess boric acid and produces a catalyst that is superior to a catalyst with an initial P/B ratio of 1.0.

Preferably fresh boron phosphate catalyst is calcined at 200° to 600° C. for 2 to 6 hours and then steam treated. It has been found that six hours of steam treatment at 275° C. removes any free boric acid from the fresh catalyst, thus precluding any plugging problems in the reactor system. It has been found that selectivity to isoprene increases with steam pretreatment of fresh catalyst, (approximately 90% vs. 80% for nonsteamed catalyst); however, 2MBA conversion decreases somewhat, but a near level 2MBA conversion is obtained. Most importantly and unexpected is the discovery that the production of methylisopropyl ketone (MIPK), the major by-product of the 2MBA dehydration reaction is less for steam treated catalysts.

It has been determined that the optimum calcination and steam treatment conditions are for a fresh catalyst: calcine at 400° C. for six hours in air (250 ml/min.) followed by steam treatment at 275° C. (2.25 LHSV) for six hours.

Steam is not recommended for use as a diluent for 2MBA dehydration catalyzed by boron phosphate.

Fresh boron phosphate catalyst pellets with a P/B ratio of 0.8 was calcined at 400° C. for six hours and then steamed for six hours at 275° C. under a very slow stream of nitrogen. Most of the free boric acid leached during the first two hours of steaming. As described herein, calcined and steam treated catalyst was placed in the reactor system and compared to a non-calcined non-steamed catalyst for 2MBA activity. The calcined and steam-stripped, fresh catalyst showed a somewhat lower, but relatively level, 2MBA conversion (approximately 20% for 24 hours). Isoprene selectivity was excellent at about 90%. The untreated, fresh catalyst provided a level conversion of about 25% and 80–80% isoprene selectivity for 24 hours.

A portion of the catalyst after calcination was placed in the reactor and tested without steam treatment. The isoprene selectivity of this calcined only, fresh catalyst was somewhat lower ( 80%), and 2MBA conversion was totally different (increased from 11% initially to 26% at the end of 24 hours). Steam stripping alone without calcination removed all the free boric acid; however, the catalyst deactivated rapidly (conversion dropped from 35 to 10% in 14 hours).

As mentioned infra, the isoprene/MIPK ratios vary with pretreatment conditions. Untreated, fresh boron phosphate, P/B of 0.8 has a ratio of 3. The calcined and then steamed fresh catalyst has a ratio of 6. Thus, steam treatment has the added advantage of increasing the isoprene/MIPK ratio.

Calcination conditions of fresh catalyst also impact on catalyst performance. Fresh catalyst calcined six hours at 450° C. deactivated slower than untreated catalyst and also produced less MIPK (isoprene/MIPK ratio of 8.5 vs. 3). Calcination of fresh catalyst (P/B of 0.8) at either 400° or 550° C. lowered the initial 2MBA conversion to about one-half when compared to an untreated catalyst (10 vs. 22%). The activity of the calcined P/B of 0.8 catalyst slowly increased with time on stream in the dehydration reaction. Initial catalyst activity was lowered as the calcination temperature was increased above 600° C. Selectivity did not change with calcination.

Using calcination temperatures and reaction temperatures as reported in the literature of 900° C. to 1000° C. respectively, it was found that the catalyst rapidly deactivated. When lower calcination temperatures were combined with lower reaction temperatures, an improved catalyst life was observed.

Through use of mild reaction and calcination temperatures, in conjunction with a hydrocarbon diluent, further catalyst life improvement was realized. A two to one ratio of 2MBA to heptane mixture was passed over a standard boron phosphate catalyst and less deactivation was observed. A one to one dilution of 2MBA with heptane gave even a lower rate of catalyst deactivation.

REACTOR SYSTEM

The data for FIGS. 1–10 was obtained from a reactor system which was a 1.25 cm by 30 cm Pyrex ™ tube and a pump system for delivery of the 2MBA. The reactor also contained a 6 cm by 2 cm preheater filled with Pyrex ™ beads. Three Pyrex ™ thermal wells were situated in the reactor, each fitted with a thermocouple; one in the preheater section, one in the first half of the catalyst bed and one in the lower half of the catalyst bed. The reactor was enclosed with fiberglass heating tapes and wrapped additionally with fiberglass tape. Manual temperature controls were used on the three separate heaters so that each portion was independently heated and controlled. The reactor was thus run under isothermal conditions.

A pump was used to charge the 2MBA feed continuously into the reactor in a downflow manner with a cocurrent nitrogen flow of 14 ml/minute. The effluent from the reactor was passed into a dry ice trap which served as the container for the reaction products. The reactor was run at atmospheric pressure. The nitrogen gas was used as a protective blanket for the catalyst, feed and effluent system. The nitrogen may also serve as a mild diluent and carrier gas although a nitrogen flow as low as 7 ml/minute changed very little in the reaction system.

The liquid hourly space velocity (LHSV) of 2MBA entering the preheater was set at 2.25 for all reactions. However, the LHSV can be varied as set out in FIG. 6. LHSV can be defined by more than one set of conditions. Therefore, as used herein, LHSV is the volume of liquid feed per hour that is passed over the total volume of catalyst. Total volume of catalyst is obtained by pouring the catalyst into a graduated cylinder to a mark of, for example, 40 cc's. The LHSV is simply calculated as follows:

$$LHSV = \frac{90 \text{ cc liquid feed/hour}}{40 \text{ cc catalyst}} = 2.25$$

The effluent (dry ice trap) from the reactor was analyzed with a gas chromatograph having a 7 meter column packed with a suitable material for resolving the components in the reaction mixture. Suitable packing materials, such as TCEP on Chromosorb P, are known to those skilled in analytical chemistry. Other conditions of the gas chromatograph were: detector temperature of 210° C., injection port temperature of 210° C., oven temperature program of 3 minutes at 70° C. followed by a 7.5° C./minute rise to 210° C. Standards were prepared and the response factors were determined for isoprene, 2-methyl-2-butene, 2-methyl-1-butene, 2-methylbutanal and methylisopropylketone with nonane as the weighed internal standard.

Since methylisopropylketone (MIPK) can be recycled to give isoprene, its wt% is added to 2MBA for percent conversion and percent selectivity for isoprene calculations. Since only the organic layer of the reaction effluent was analyzed, the weight of water produced must be calculated from the wt% of isoprene. The following mathematical adjustment was used:

(Weight % Isoprene) (Sample Weight) = Weight of Isoprene
(Weight of Isoprene) (18/68) = Weight of Water
Sample Weight + Weight of Water = Real Sample Weight
(100) (Weight of Water/Real Sample Weight) =
   Real Weight % of Water
Thus,
(Weight % Isoprene) (Sample Weight/Real Sample Weight)=
   Real Weight % Isoprene; and
(Weight % 2 MBA + MIPK)
   (Sample Weight/Real Sample Weight) =
      Real Weight % 2MBA; then % 2MBA Conversion =

$$\frac{(\% \text{ Purity of 2MBA} - \text{Real Weight \% 2MBA})}{(\% \text{ Purity of 2MBA})} \times 100;$$

% Isoprene Selectivity =

$$\frac{(\text{Real Wt. \% Isoprene} + \text{Real Wt. \% Water})}{(100 - \text{Real Weight \% 2MBA})} \times 100$$

The 2MBA feed should be at least 90% pure. Other compounds in the 2MBA feed may include various by-products from the reaction of 2-butene and syngas to produce the 2MBA such as 2-methylbutyric acid. Other compounds such as n-pentanal may also be present in minor amounts.

Typical analysis of the effluent from the reactor using a catalyst of the invention after laboratory-scale fractionation had the following approximate product composition:

| Component | Weight % |
|---|---|
| Lights | 0.7 |
| 1-Pentene | 0.1 |
| 2-methly-1-butene | 2.3 |
| trans-2-Pentene | 0.3 |
| cis-2-Pentene | 0.3 |
| 2-methyl-2-butene | 6.2 |
| Isoprene | 89.6 |
| Other | 0.5 |

Analysis indicated no acetylenics; however, cyclopentadiene (CPD) was present at a concentration of 15 ppm (parts per million). The amount of CPD was found to decrease with continuous on-stream time and usually ranged from about 20 to 30 ppm CPD at the outset of reaction to about 4 ppm after 24 hours on stream.

POLYMERIZATION OF PRODUCED ISOPRENE

The reactor effluent after fractionation and CPD removal via KOH treatment was used as a monomer to produce 1,4-polyisoprene using standard polymerization techniques. The isoprene polymerized in an acceptable manner and produced a polymer of expected properties.

GRAPHITE LOADING

One aspect of the present invention is the incorporation of graphite with the boron phosphate catalyst. It has been unexpectedly discovered that an admixture of graphite to the boron phosphate catalyst results in extended catalyst lifetimes over catalysts that do not contain graphite.

The graphite provides a decrease in the rate of deactivation of the catalyst during the dehydration of 2MBA to isoprene.

The graphite may be incorporated by mixing with sieved boron phosphate until a uniform coating is obtained, by mixing with powdered boron phosphate followed by pelletizing or by adding the graphite to the boron phosphate paste during the preparation of the catalyst.

A boron phosphate catalyst was prepared and half was mixed with graphite at a level of 2.5 wt% and placed in the reactor as described above. The remaining half was used as a control. The boron phosphate had a P/B ratio of 0.8 and the dehydration was conducted at 275° C. and an LHSV of 2.25. The conversion, selectivities and deactivation rate are set out in FIG. 3. FIG. 7 also sets out the conversion and selectivities for at P/B of 0.8 and graphite of 1.25 weight %. For commercialization of catalysts, a relatively level and high selectivity is desirable. FIG. 8 sets out an experiment wherein HAF carbon black is used without benefit.

INDUSTRIAL APPLICABILITY

As demand for isoprene increases and the supply from petroleum feedstocks decrease, there will be a need for alternative methods of obtaining isoprene. The instant invention provides a process that utilizes a catalyst that overcomes the limitations previously found in the dehydration of 2MBA to isoprene. Thus, the industry now has a catalyst that is superior to the catalysts previously used. It is the unexpected and unobvious use of a boron phosphate catalyst as described and claimed herein that provides an advancement in the art of converting aldehydes to dienes.

Although the present invention has been described herein with reference to the preferred typical embodiments thereof, it will be apparent to those skilled in the art that there may be modifications made in the process hereof.

We claim:

1. A process for the conversion of 2-methylbutanal (2MBA) to isoprene which comprises contacting 2MBA in the vapor phase at a temperature of from 200° to 400° C. with a boron (B) phosphate (P) catalyst, the improvement characterized in that
(1) the boron phosphate catalyst is prepared by
 (a) combining phosphoric acid and boric acid and/or trialkylborate, wherein the alkyl group is from 1 to 6 carbon atoms;
 (b) at such molar ratios that the molar ratio of P/B is less than 1.0 but more than 0.6;
 (c) contacting the boron phosphate with from 0 to 10 mole percent based on moles of boron, ammonia or an amine, selected from the group consisting of mono-, di- and/or tri-alkyl amines wherein the alkyl group is from 1 to 10 carbon atoms;
 (d) admixing the boron phosphate with from 0.1 to 10 weight percent graphite based on total weight of the boron phosphate;
 (e) calcining the boron phosphate in air at a temperature of from 250° to 650° C. for 1 to 6 hours;
 (f) steaming the calcined boron phosphate at 200° to 300° C. for ½ to 10 hours;
(2) the 2MBA feed is diluted with from 0 to 80 weight percent from a solvent selected from the group consisting of pentane, hexane, heptane, octane and nonane; and
(3) the 2MBA is charged to the reactor at an LHSV of from 1.0 to 20.

2. A process according to claim 1 wherein the molar ratio of P/B can range from 0.75 to 0.98.

3. A process according to claim 1 wherein the boron phosphate is prepared using tripropyl borate.

4. A process according to claim 1 wherein the boron phosphate catalyst contains from 2.0 to 5.0 weight percent graphite.

5. A process according to claim 1 wherein the 2MBA feed is diluted on a one to one weight basis with heptane.

6. A process for the conversion of an aldehyde of 4 to 6 carbon atoms to the corresponding diene which comprises contacting the aldehyde in the vapor phase at a temperature of from 200° to 400° C. with a boron phosphate catalyst, said catalyst characterized in that the initial molar ratio of phosphorous (P) to boron (B) (P/B) is less than 1.0 but more than 0.6, is in physical admixture with from 0.1 to 10 weight percent graphite, has been calcined at a temperature from 300° to 500° C. for 2 to 6 hours in air and has been steam treated at from 225° to 300° C. for at least half an hour at an LHSV of at least 2.0.

7. A process for the conversion of an aldehyde of 4 to 6 carbon atoms to the corresponding diene which comprises passing the aldehyde in the vapor phase over a boron phosphate dehydration catalyst, the improvement comprising: a catalyst which has an initial molar ratio of P/B of less than 1.0 but more than 0.6 which is in admixture with from 0.1 to 10 weight percent graphite.

8. A process according to claim 6 wherein the aldehyde is 2-methylbutanal, the diene is isoprene, the temperature is from 275° to 350° C., the P/B molar ratio is from 0.8 to 0.7, and the weight percent graphite is from 2.0 to 5.0.

9. A process according to claim 6 wherein the temperature is from 300° to 350° C., and the weight percent graphite is 2.5.

10. A process according to claim 6 wherein the initial P/B molar ratio is 0.8 to 0.7, and the weight percent graphite is 2.5.

11. A process according to claim 7 wherein the initial P/B molar ratio is 0.8 to 0.7, and the weight percent graphite is 2.5.

* * * * *